United States Patent [19]

Cassou et al.

[11] Patent Number: 5,545,562
[45] Date of Patent: Aug. 13, 1996

[54] DEVICE FOR IDENTIFYING STRAWS FOR CRYOGENIC STORAGE OF BIOLOGICAL LIQUIDS

[75] Inventors: Robert Cassou, Sainte Montaine; Maurice Cassou; Bertrand Cassou, both of L'Aigle, all of France

[73] Assignee: Instruments de Medecine Veterinaire, L'Aigle, France

[21] Appl. No.: 460,391

[22] Filed: Jun. 2, 1995

Related U.S. Application Data

[63] Continuation of Ser. No. 251,354, May 31, 1994, abandoned.

[51] Int. Cl.⁶ .................................................. C12M 1/24
[52] U.S. Cl. .................. 435/307.1; 422/102; 422/119
[58] Field of Search ........................ 40/316; 422/99, 422/119, 102; 435/1, 2, 284, 287, 296, 307.1

[56] References Cited

U.S. PATENT DOCUMENTS

| | | | |
|---|---|---|---|
| 1,298,981 | 4/1919 | Loughridge | 40/316 |
| 3,212,207 | 10/1965 | Searing | 40/316 |
| 3,491,472 | 1/1970 | Walldorf | 40/316 |
| 5,190,880 | 3/1993 | Cassou et al. | 435/296 |

*Primary Examiner*—Jeffrey R. Snay
*Attorney, Agent, or Firm*—Longacre & White

[57] ABSTRACT

A device for identifying the content of a straw formed of a heat-sealed section of ionomer resin tube offering high performance at cryogenic temperatures comprises a sheath length threaded onto the straw and trapped between the ends of the straw which are flattened and widened in the transverse direction on sealing the straw after filling. The sheath carries printed identifying data and its color facilitates identification. This avoids the possibility of defective printing on the ionomer resin and damage to the straw or its contents by diffusion of constituents of the ink. The sheath can be ovalized at one end to prevent it moving freely.

10 Claims, 1 Drawing Sheet

DEVICE FOR IDENTIFYING STRAWS FOR CRYOGENIC STORAGE OF BIOLOGICAL LIQUIDS

This is a continuation of application Ser. No. 08/251,354, filed May 31, 1994, which was abandoned upon the filing hereof.

BACKGROUND OF THE INVENTION

1. Field of the Invention

The invention concerns a device for identifying tubes known as straws for cryogenic storage of biological liquids, such as viral cultures, and including an envelope formed by a section of appropriate transparent material tube of constant diameter in the main part with its ends flattened to form welded seals wider than the diameter of the main part.

2. Description of the Prior Art

Patent document FR-A-2 651 793 describes a tube called a straw for cryogenic storage of biological samples, such as viral cultures, formed by a section of constant diameter tubular envelope made from a biologically neutral substantially transparent polymer material sealed at each end and including near a first end a sliding stopper comprising an aqueous gel between two porous elastic material plugs, distinguished from the prior art in that the polymer material is an ionomer resin and the seals at the ends are formed by welding the tube over a specific axial length.

By virtue of the physical properties of ionomer resins, including their thermoplastic behavior at room temperature and higher temperatures, allowing an excellent seal by welding, resistance to thermal shock between room temperature and cryogenic temperatures and freedom from fragilization at these temperatures, these straws are extremely reliable for the cryogenic storage of rare or dangerous biological liquids such as viruses and the products of genetic engineering.

However, it has been found that ionomer resins, especially those with particularly attractive properties at cryogenic temperatures, are more difficult to print on than materials used for manufacturing straws used on a large scale (such as the straws used for artificial insemination of cattle and sheep), the constituents of the printing inks used diffusing less readily into ionomer resins, with the result that the printed characters are not so clear and more easily rubbed off.

Furthermore, even if these ink constituents diffuse less readily into ionomer resins, there remains the risk that diffusion of solvent through the thin wall (which is only a few tenths of a millimeter thick) could interfere with the biological liquid or that diffusion of solvent into the thickness of the wall could compromise the properties of the ionomer resin at cryogenic temperatures.

When the rarity of the biological liquid samples or the associated level of hazard make it necessary to reduce the number of straws containing the same biological liquid, it is desirable to make the straws more distinctive to reduce the frequency of errors through making the wrong choice. All the more so in that one effect of cryogenic storage is to cause the straws to be covered with frost as soon as they are removed from the liquid nitrogen, so that they are difficult to identify from the printed markings alone.

SUMMARY OF THE INVENTION

The invention consists in a device for identifying tubes known as straws used for cryogenic storage of biological liquids, such as viral cultures, and including an envelope formed by a section of appropriate transparent material tube with a constant diameter in its main part and its ends flattened to form welded seals wider than the diameter of the main part, the device comprising a length of polymer material sheath adapted to support identifying signs with an inside diameter less than the width of the seals and threaded over the tube section between the end seals.

The sheath length is thus trapped between the seals at the two ends of the straw and so cannot escape until one sealed end has been cut off.

In other words, the sheath is fitted at the same time as the content of the straw is sealed in and cannot be removed from the straw unless one end is cut off to extract the contents.

The sheath length may be made from a material which is readily printed and which is able to constitute an identification element by virtue of its inherent appearance. There is no risk of the constituents of the printing ink on the sheath migrating into the material of the straws.

The identifying signs can include printed characters, color coding of the sheath material or even a length ratio between the straw and the sheath.

In a preferred embodiment, the sheath diameter being sufficient in itself to allow sliding under its own weight, the sheath is deformed at one end to grip the tube elastically at at least two points that are diametrically opposed. It is still easy to fit the sheath before the ends are sealed, but once the deformed end is engaged with the straw the sheath will be fixed in position on the straw. It would be difficult to identify the straw if the sheath length could slide freely along the straw and so slide down towards the lower end of the straw upon insertion of the latter into the cryogenic vessel, which is necessarily done from the top of the vessel.

Secondary features and advantages of the invention emerge from the following description given by way of example with reference to the appended drawings.

DETAILED DESCRIPTION OF THE PREFERRED EMBODIMENT

Figure 1A:
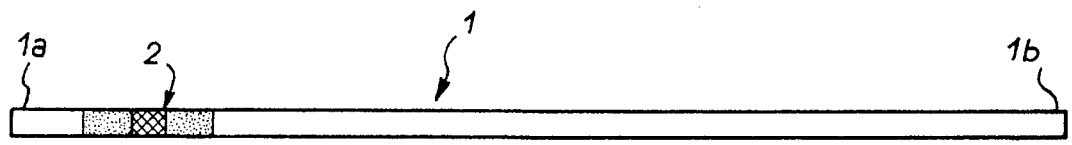
FIG. 1A shows a straw before it is filled.

In the chosen embodiment shown in the figures a tube or straw 1 is initially, as shown in FIG. 1A, in the form of a section of tube having a constant outside diameter over its main part, open at both ends 1a and 1b and made from an ionomer resin as described in document FR-A-2 651 793. Near the end 1a is a sliding stopper as described in document FR-A-995 878 (10 Dec. 1951). The stopper is a quantity of powder adapted to gel in contact with an aqueous liquid between two porous plugs.

Figure 1B:
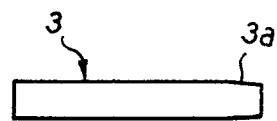
FIG. 1B shows an identifying sheath according to the invention.
Figure 2:
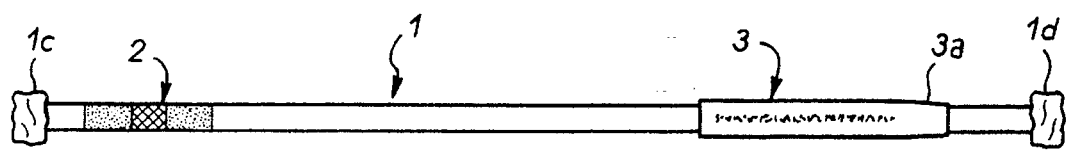
FIG. 2 shows a filled and sealed straw fitted with an identifying sheath.
Figure 3:
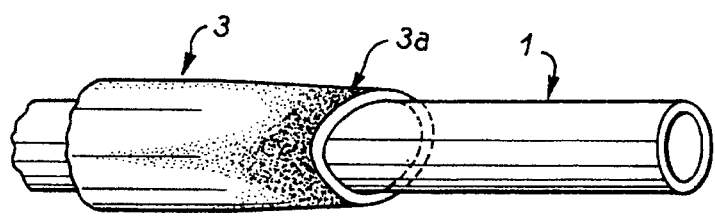
FIG. 3 shows in perspective a detail of how the sheath is immobilized on the straw.
Figure 4:
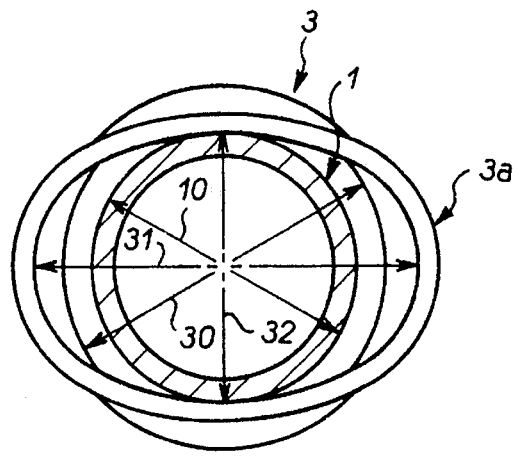
FIG. 4 is an end view showing the mounting of the sheath on the straw.

A sheath length 3 (FIG. 1b) is prepared with an inside diameter 30 (see FIG. 4) greater than the outside diameter 10 of the straw 1, its length being approximately equal to one third that of the straw 1. The sheath 3 is made from a readily extruded thermoplastics material such as polyvinyl chloride and is self-colored. As seen clearly in FIGS. 3 and 4, the sheath 3 is ovalized at one end 3a by stretching it in the direction of a major axis 31 so that its minor axis 32, when unstressed (FIG. 1b), is slightly shorter than the outside diameter 10 of the straw 1.

Immediately before the straw 1 is filled the chosen color of sheath length 3 has its outside surface printed with data identifying the biological liquid with which the respective straw 1 is to be filled; the color of the sheath constitutes an identifying element, in addition to the printed data, in order to allow selection from the cryogenic storage vessel at a glance, subject to subsequent verification of the printed data, of course.

When printed, the sheath length 3 is threaded over the straw, starting with the end opposite the ovalized end 3a. The end 1b of the straw is allowed to protrude at least one centimeter.

The straw 1 fitted with its identifying sheath is then taken to a filling machine where the biological liquid that the straw is to contain is sucked into it through the end 1a and through the stopper 2. When the biological liquid reaches the stopper it gels the powder and seals the stopper, in the known way.

After filling, the ends 1a and 1b are sealed by clamping them between two parallel plane heated jaws. The welded ends are formed into spatulas 1c and 1d whose width perpendicular to the axis of the straw exceeds the inside diameter 30 and the length of the major axis 31 of the ovalized end 3a of the sheath length 3. The latter is accordingly trapped between the sealed ends 1c and 1d of the straw until one end is cut off to extract the contents of the straw.

Note that there is no disadvantage in the sheath having less desirable properties than ionomer resins at cryogenic temperatures, as it is not subject to any mechanical stress and does not play any role in the reliable storage of the product. Even cracking of the sheath is immaterial.

It will have been realized that the ovalization 3a of the sheath length 3 is intended to prevent the sheath 3 sliding along the straw 1 so that the sheath and the identifying data on it remain clearly visible during storage at cryogenic temperature without impeding in any way the fitting of the sheath 3 around the straw 1. It goes without saying that the sheath 3 could be immobilized on the straw 1 by any manner procuring localized gripping of the straw by the sheath at at least two diametrally opposed points. In point of fact, immobilization of the sheath 3 on the straw is not strictly essential to its identifying function, although this function is facilitated by immobilizing the sheath.

The sheath length 3 threaded onto the straw is limited only by the necessity to leave the ends 1a and 1b of the straw exposed in order to seal them. However, it is beneficial to leave at least some length of the straw uncovered near the ends to facilitate the use of conveyor racks at the filling machine and to facilitate cutting off of the ends to recover the contents. It is preferable for at least half the length of the straw 1 to remain uncovered to enable visual inspection of the contents. However, a sheath length 3 less than one quarter the length of the straw 1 may provide insufficient room for printing identifying data.

These considerations confirm that the invention is not limited to the embodiments described but encompasses all variant executions thereof within the scope of the claims.

There is claimed:

1. A straw for cryogenic storage of biological liquids comprising a tubular envelope of transparent material having a main part of substantially uniform diameter and flattened welded ends having a width greater than the diameter of the main tube section, an identification sheath of polymer material for carrying identification markings relative to the biological liquid received on said main part, said sheath having an end portion elastically gripping the main tube section with an inside diameter less than the diameter of said main tube section whereby said welded ends prevent removal of said sheath from said straw prior to severing of one of said welded ends to extract the biological liquid, said sheath also having a longitudinally extending portion having a minimum transverse dimension greater than the diameter of the outer diameter of the main tube section so as to be loosely received around said main tube section.

2. A straw according to claim 1, wherein said identification markings are printed on said sheath.

3. A straw according to claim 1, wherein said identification markings comprise color coding of the polymer material of said sheath.

4. A straw according to claim 1, wherein said end portion of said sheath locally elastically grips said tube section to maintain said sheath in position on said straw.

5. A straw according to claim 1, wherein the length of said sheath is less than half the length of said straw.

6. A straw according to claim 5, wherein the length of said sheath is greater than one quarter the length of the straw.

7. A straw according to claim 1, wherein said longitudinally extending portion of said sheath comprises a major part of the length of the sheath.

8. A straw according to claim 7, wherein said sheath has an opposite end portion remote from the first mentioned end portion, said first mentioned end portion having an ovalized section, the distance between zones lying along a minor axis of the ovalized section being less than the outer diameter of the main tube section of said straw so as to elastically locally grip said straw.

9. A combination of an identification device and a straw for cryogenic storage of biological liquids comprising a tubular envelope of transparent material having a tubular section of constant diameter, said identification device comprising a sheath of polymer material for carrying identification markings relative to the biological liquid adapted to be received on the main tubular section of the straw, means for locally elastically gripping said tube section located at one end portion of said sheath, an opposite end portion remote from said one end portion and a major part of the length of said sheath having a minimum transverse dimension substantially greater than the outer diameter of the straw main tube section so as to be loosely received around said tubular section.

10. The combination according to claim 9, wherein said one end portion is of ovalized shape, said means for locally elastically gripping the tube section comprising first diametrically opposed zones of the ovalized end portion of said sheath, said zones lying along a minor axis of the ovalized end portion of said sheath, the distance between said opposed zones, when unstressed, being less than the distance between second diametrically opposed zones lying along a major axis of the ovalized end portion.

* * * * *